(12) United States Patent
Lou et al.

(10) Patent No.: US 11,459,593 B2
(45) Date of Patent: Oct. 4, 2022

(54) *DENDROBIUM OFFICINALE* ENDOPHYTIC FUNGUS STRAIN AND EXTRACELLULAR POLYSACCHARIDE PRODUCED THEREBY, AND EXTRACTION METHOD AND APPLICATION OF EXTRACELLULAR POLYSACCHARIDE

(71) Applicant: SOUTH CHINA UNIVERSITY OF TECHNOLOGY, Guangzhou (CN)

(72) Inventors: Wenyong Lou, Guangzhou (CN); Yingjie Zeng, Guangzhou (CN); Hongfeng Wang, Guangzhou (CN); Minhua Zong, Guangzhou (CN); Jing Liang, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 270 days.

(21) Appl. No.: 16/604,238

(22) PCT Filed: Dec. 13, 2017

(86) PCT No.: PCT/CN2017/115762
§ 371 (c)(1),
(2) Date: Oct. 10, 2019

(87) PCT Pub. No.: WO2019/000850
PCT Pub. Date: Jan. 3, 2019

(65) Prior Publication Data
US 2020/0157590 A1    May 21, 2020

(30) Foreign Application Priority Data
Jun. 29, 2017 (CN) .......................... 201710512714.4

(51) Int. Cl.
| | | |
|---|---|---|
| *C12P 19/04* | (2006.01) | |
| *A01N 63/30* | (2020.01) | |
| *C08B 37/00* | (2006.01) | |
| *C12N 1/14* | (2006.01) | |
| *C12R 1/77* | (2006.01) | |

(52) U.S. Cl.
CPC ............. *C12P 19/04* (2013.01); *A01N 63/30* (2020.01); *C08B 37/0003* (2013.01); *C12N 1/145* (2021.05); *C12R 2001/77* (2021.05)

(58) Field of Classification Search
CPC . C12R 2001/77; C08B 37/0003; C12N 1/145; A01N 63/30; C12P 19/04
See application file for complete search history.

(56) References Cited

FOREIGN PATENT DOCUMENTS

| CN | 104630073 A | 5/2015 |
| CN | 104450541 A | 8/2017 |
| CN | 107245457 A | 10/2017 |
| CN | 105886405 A | 6/2019 |

OTHER PUBLICATIONS

Zeng et al., "Structure and immunomodulatory activity of polysaccharides from Fusarium solani D07 by solid-state fermentation" International Journal of Biological Macromolecules vol. 137 pp. 568-575 (Year: 2019).*
Sun, Y., Wang, H., Guo, G., Pu, Y., & Yan, B. (2014). The isolation and antioxidant activity of polysaccharides from the marine microalgae *Isochrysis galbana*. Carbohydrate polymers, 113, 22-31. (Year: 2014).*
Jin, M., Wang, Y., Xu, C., Lu, Z., Huang, M., & Wang, Y. (2010). Preparation and biological activities of an exopolysaccharide produced by Enterobacter cloacae Z0206. Carbohydrate Polymers, 81(3), 607-611. (Year: 2010).*
Angelis, S. D., Novak, A. C., Sydney, E. B., Soccol, V. T., Carvalho, J. C., Pandey, A., . . . & Soccol, C. R. (2012). Co-culture of microalgae, cyanobacteria, and macromycetes for exopolysaccharides production: process preliminary optimization and partial charact (Year: 2012).*
Mahapatra, S., & Banerjee, D. (2013). Optimization of a bioactive exopolysaccharide production from endophytic Fusarium solani SD5. Carbohydrate polymers, 97(2), 627-634 (Year: 2013).*

* cited by examiner

*Primary Examiner* — Louise W Humphrey
*Assistant Examiner* — Trevor L Kane
(74) *Attorney, Agent, or Firm* — Troutman Pepper Hamilton Sanders LLP; Christopher C. Close, Jr.

(57) ABSTRACT

The present invention provides a *Dendrobium officinale* (*D. officinale*) endophytic fungus strain and an extracellular polysaccharide produced thereby as well as an extraction method and application of the extracellular polysaccharide. The extraction process of the extracellular polysaccharide includes: activating a strain; culturing seed liquid; fermenting and culturing; filtering the fermented liquid under vacuum; concentrated the filtrate under vacuum; conducting alcohol precipitation on the concentrated liquid; precipitating and centrifuging; dialyzing after dissolving the precipitates in water; freezing and drying the dialysate under vacuum; and obtaining the extracellular polysaccharide. The *D. officinale* endophytic fungus strain belongs to *Fusarium solani*, and the extracellular polysaccharide produced thereby has inhibitory effects on *Escherichia coli*, *Staphylococcus aureus*, *Salmonella* ssp., and *Bacillus subtilis*.

6 Claims, 5 Drawing Sheets

Specification includes a Sequence Listing.

DENDROBIUM OFFICINALE ENDOPHYTIC FUNGUS STRAIN AND EXTRACELLULAR POLYSACCHARIDE PRODUCED THEREBY, AND EXTRACTION METHOD AND APPLICATION OF EXTRACELLULAR POLYSACCHARIDE

TECHNICAL FIELD

The present invention relates to the field of extraction of a polysaccharide from an endophytic fungus strain, and specifically to a *Dendrobium officinale* endophytic fungus strain and an extracellular polysaccharide produced thereby as well as an extraction method and application of the extracellular polysaccharide.

BACKGROUND

Plant endophytic fungi refer to those fungi that live in a variety of tissues and organs of a healthy plant at certain or all stages of their life histories. Different from mycorrhizal fungi only present in plant roots, endophytic fungi are present in any tissues and organs of both aerial and underground parts of a plant. It has been found that: plant endophytic fungi include mutually beneficial and neutral endophytic fungi, as well as those pathogens that lurk in a host; some endophytic fungi promote host plant growth, enhance host stress resistance, and facilitate the synthesis and accumulation of active ingredients of the host plant, playing an active role in improving plant yield and quality. Therefore, it is of tremendous potentiality to utilize plant endophytic fungi, a treasure that has not been deeply explored, and to screen active substances thereby; not only do secondary metabolites synthesized comprise abundant chemical constituents, but are also characterized by a variety of bioactivities. It is of great significance to isolate endophytic fungi from *Dendrobium officinale*, a traditional medicinal plant and a host, and investigate fungal activities thereof.

*Dendrobium officinale* Kimura et Migo (*D. officinale*), an epiphytic orchid herb, is a valuable, traditional Chinese medicinal material that is effective in nourishing yin and clearing heat, tonifying stomach and promoting fluid, moistening lungs and improving eyesight, anticancer and anti-aging; topping the list of nine major miraculous herbs of China, *D. officinale* is widely applied in prescriptions for chronic pharyngitis, occlusive peripheral angiopathy, cataract and glaucoma as well as a variety of health products. There has been no available wild resource owing to resource exhaustion by great market demand and chronically unlicensed excavation. By 1987, *D. officinale* was listed as a national key protected wild plant, has been listed as endangered in *China Plant Red Data Book*, and has been a national Class II protected plant. In *Pharmacopoeia of the People's Republic of China* 2010 Edition, *D. officinale* was separated from *Dendrobium* medicinal materials and included solely.

Over the past two decades, owing to studies regarding chemical functions of membrane and immune substances as well as search for new drug resources, it has found that polysaccharide serves as an energy resource or a structural material in an organism, and what is more, it involves in a variety of cellular activities in life science and exhibits all kinds of biological and active functions, e.g., hypoglycemic, antihyperlipidemic, cardio-cerebrovascular protective, anti-tumor, antibacterial, antiviral, immunopotentiating or immunomodulatory, liver-, intestine- and stomach-protecting, anti-inflammatory, antioxidative, and anti-aging effects.

SUMMARY

An objective of the present invention is to provide a *Dendrobium officinale* (*D. officinale*) endophytic fungus strain, which belongs to *Fusarium solani* and is isolated and purified from a living *D. officinale* plant by endophytic fungus isolation and purification technique.

An objective of the present invention is to further provide an extracellular polysaccharide produced by the *D. officinale* endophytic fungus strain, and the extracellular polysaccharide produced thereby has a good inhibitory effect on pathogens.

An objective of the present invention is to further provide an extraction method of the extracellular polysaccharide produced by the *D. officinale* endophytic fungus strain. The method includes the following process: activating a strain; culturing seed liquid; fermenting and culturing; filtering the fermented liquid under vacuum; concentrated the filtrate under vacuum; conducting alcohol precipitation on the concentrated liquid; precipitating and centrifuging; dialyzing after dissolving the precipitates in water; freezing and drying the dialysate under vacuum; and obtaining a freeze-dried powder, i.e., the extracellular polysaccharide.

An objective of the present invention is to further provide an application of the extracellular polysaccharide produced by the *D. officinale* endophytic fungus strain in pathogen inhibition.

The objectives of the present invention are achieved through the following technical solutions.

A *D. officinale* endophytic fungus strain, belonging to *Fusarium solani*, named *Fusarium solani* DO7, was preserved at China Center for Type Culture Collection (CCTCC) (Wuhan University, Luojia Hills, Wuchang Road, Wuhan, Hubei Province 430072) on Mar. 27, 2017 with the accession number of CCTCC NO. M2017145.

An extraction method for the extracellular polysaccharide produced by the *D. officinale* endophytic fungus strain includes the following steps:

(1) activating the *D. officinale* endophytic fungus strain, culturing seed liquid, and then fermenting and culturing the obtained seed liquid; and (2) filtering the fermented liquid obtained after the fermenting and culturing in step (1) under vacuum; conducting vacuum concentration, alcohol precipitation and centrifugation on a filtrate obtained; dehydrating and drying centrifuged precipitates, dissolving in deionized water for dialysis, and freezing and drying the dialysate under vacuum, to obtain the extracellular polysaccharide produced by the *D. officinale* endophytic fungus strain.

Further, in step (1), the activating and culturing is to use a slant culture method for activation in a test tube for 48-72 hours at 28±1° C., with potato dextrose agar (solid PDA) as a medium.

Further, in step (1), the culturing seed liquid is to incubate in a potato dextrose broth (PDB) medium for 48-72 hours on a shaking table at 28±1° C. and 120 rpm.

Further, in step (1), the fermenting and culturing is to inoculate 5%-15% (v/v) of the seed liquid in a PDB medium and fermente and culture for 7-14 days on a shaking table at 28±1° C. and 120 rpm.

Further, in step (2), the vacuum concentration is to concentrate the filtrate to $\frac{1}{10}$ of the volume of stock solution in a rotary evaporator at 45° C.

Further, in step (2), the alcohol precipitation is to mix the concentrated liquid well with 95% ethanol (v/v) at a volume ratio of 1:4 and standing for 12-24 hours at 4° C.

Further, in step (2), the centrifugation is to centrifuge for 15 minutes at 8000 rpm.

Further, in step (2), the dehydrating is to wash with absolute ethanol, acetone and petroleum ether sequentially.

Further, in step (2), the drying is performed at 50-55° C.

Further, in step (2), a concentration range is 0.05-0.2 g/mL for dehydrated and dried precipitates dissolved in deionized water.

Further, in step (2), the dialyzing is to dialyze with a dialysis bag with a molecular weight cutoff of 3500 Da against distilled water for 24-72 hours.

An extracellular polysaccharide produced by the *D. officinale* endophytic fungus strain is obtained by the extraction method according to any preceding step.

The extracellular polysaccharide extracted has good antibacterial activity and has significantly inhibitory effects on pathogens including *Escherichia coli, Staphylococcus aureus, Salmonella* ssp., and *Bacillus subtilis*. The extracellular polysaccharide produced by the *D. officinale* endophytic fungus strain is applied in pathogen inhibition.

Compared with the prior art, the present invention has the following advantages and beneficial effects:

(1) the extracellular polysaccharide produced by the *D. officinale* endophytic fungus strain in the present invention has significantly inhibitory effects on pathogens including *E. coli, S. aureus, Salmonella* ssp., and *B. subtilis* and is well applicable in pathogen inhibition; and (2) the extraction method of the present invention has a simple and feasible process, mild conditions, and ease of control, provides a new way to extract the extracellular polysaccharide produced by the *D. officinale* endophytic fungus strain on a large scale and also provides a new idea for increasing extracellular polysaccharide yield by improving the interaction between endophytic fungus and host plant.

DETAILED DESCRIPTION

Figure 1:
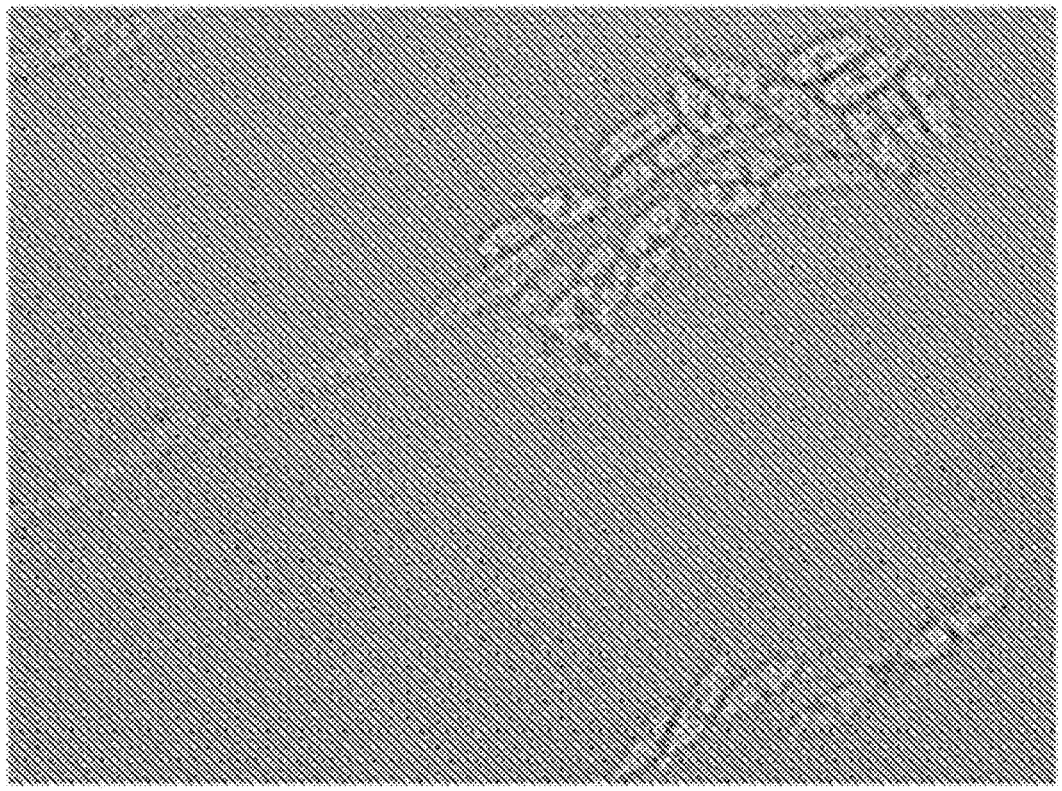
FIG. 1 is a morphological image of hyphae of a *Dendrobium officinale* (*D. officinale*) endophytic fungus strain, *Fusarium solani* DO7, grown in PDA medium for five days in Embodiment 1, observed under microscope at 100-fold magnification.

The technical solutions of the embodiments of the present invention will be further elaborated in combination with specific embodiments and accompanying drawings, but the invention is not limited thereto.

The experimental methods without any specific conditions in the following embodiments are usually in accordance with the conventional conditions or conditions as specified in a Laboratory Manual or as recommended by manufacturers.

A specific embodiment of the present invention provides a *Dendrobium officinale* (*D. officinale*) endophytic fungus strain, belonging to *Fusarium solani*, named *Fusarium solani* DO7, preserved at China Center for Type Culture Collection (CCTCC) (Wuhan University, Luojia Hills, Wuchang Road, Wuhan, Hubei Province 430072) on Mar. 27, 2017 under CCTCC NO. M2017145;

SEQ ID No. 1 shows rDNA internal transcribed spacers (ITSs) and 5.8S rRNA-encoding genes of the *D. officinale* endophytic fungus strain, *Fusarium* DO7.

A specific embodiment of the present invention provides an extracellular polysaccharide produced by the *D. officinale* endophytic fungus strain, including the following extraction process:

activating a strain; culturing seed liquid; fermenting and culturing; filtering the fermented liquid under vacuum; concentrated the filtrate under vacuum; conducting alcohol precipitation on the concentrated liquid; precipitating and centrifuging; dialyzing after dissolving the precipitates in water; freezing and drying the dialysate under vacuum; and obtaining a freeze-dried powder, i.e., the extracellular polysaccharide.

The extracellular polysaccharide obtained is dissolved in distilled water, and then the extracellular polysaccharide content is assayed by phenol-sulphuric acid colorimetry as specified in *Pharmacopoeia of the People's Republic of China* 2010 Edition, Volume I.

A specific embodiment of the present invention provides an extracellular polysaccharide produced by the *D. officinale* endophytic fungus strain, having significantly inhibitory effects on pathogens including *Escherichia coli, Staphylococcus aureus, Salmonella* ssp., and *Bacillus subtilis*. Assessment of antibacterial activity comprises the following process:

activating pathogen strain; culturing seed liquid; performing a spread plate method; inoculating filter paper containing the extracellular polysaccharide produced by the strain; culturing; and observing antibacterial results;

Specific assessment of antibacterial activity includes the following steps:

(1) using a slant culture method to activate and culture a pathogen strain for 24 hours at 37±1° C., with the medium being a beef extract-peptone agar medium (solid LB medium);

(2) transferring the activated strain into the beef extract-peptone agar medium (LB liquid medium) and incubating for 24 hours on a shaking table at 37±1° C. and 160 rpm to obtain seed liquid;

(3) inoculating the seed liquid obtained onto a spread-plate medium (with beef extract-peptone agar medium or beef extract broth-peptone medium), coagulating, and then culturing for 24 hours at 37±1° C.; and (4) using a hole puncher with a diameter of 6 mm to obtain filter paper, sterilizing the filter paper and immersing it in 0.05 g/l extracellular polysaccharide solution, air drying, placing into a Petri dish containing a well-cultured test strain, inverting a plate and culturing for 24-48 hours at 37° C.

Embodiment 1

A solid culture of a *Dendrobium officinale* (*D. officinale*) endophytic fungus strain, *Fusarium solani* DO7 is characterized in that:

aerial hyphae vary in color from colorless initially to red gradually after culturing in PDA medium for 4-7 days at 28±1° C.; colonies appear light white and villiform, with irregular edge; hyphae are white and developed, which dorsally vary in color from white initially to red gradually.

Figure 2A:
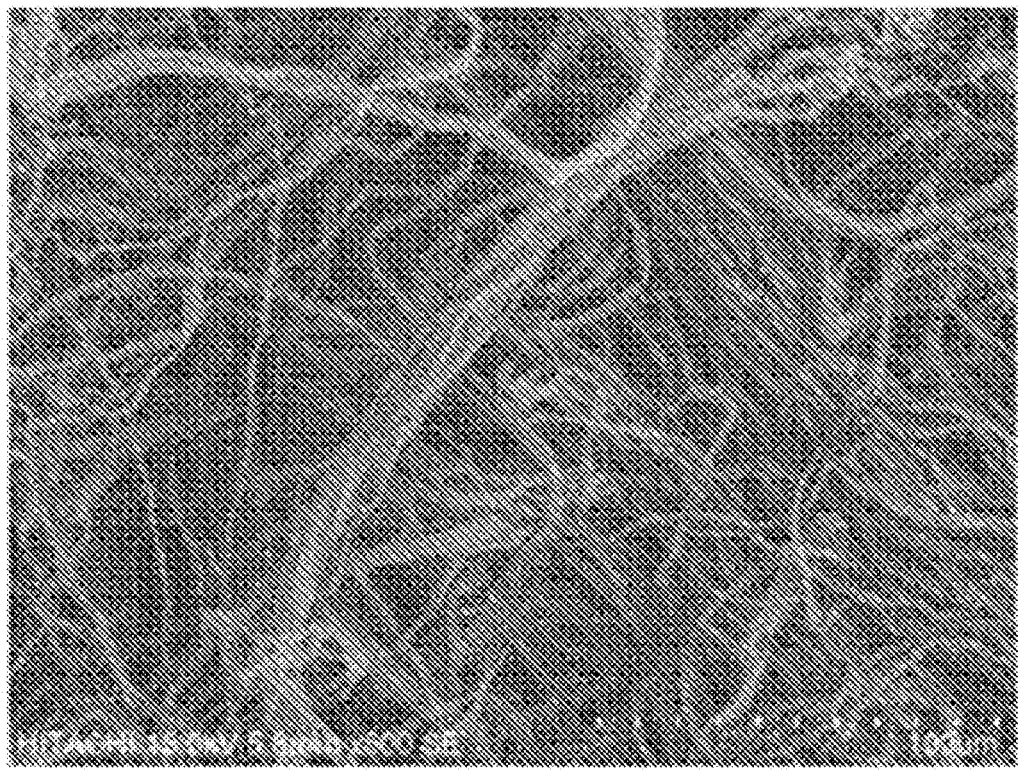
FIGS. 2A and 2B are morphological images of hyphae of the *D. officinale* endophytic fungus strain, *Fusarium solani* DO7, grown in PDA medium for five days in Embodiment 1, observed under scanning electron microscope (SEM) at different magnifications.
Figure 2B:
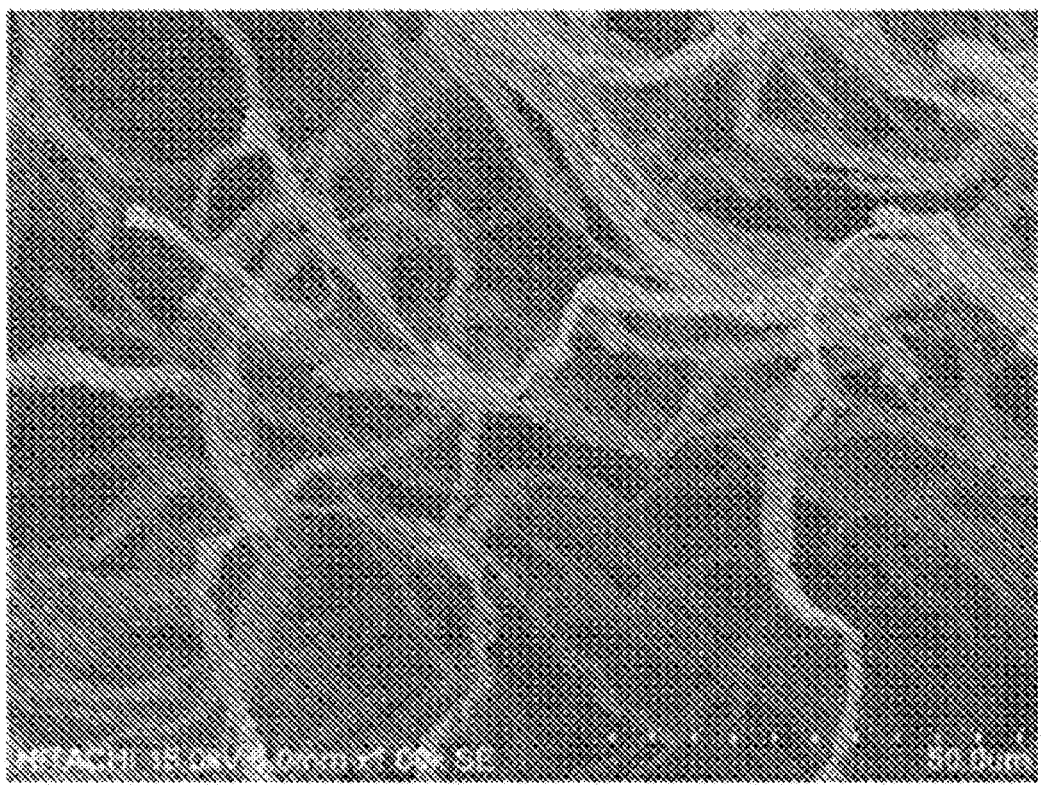
Figure 3A:
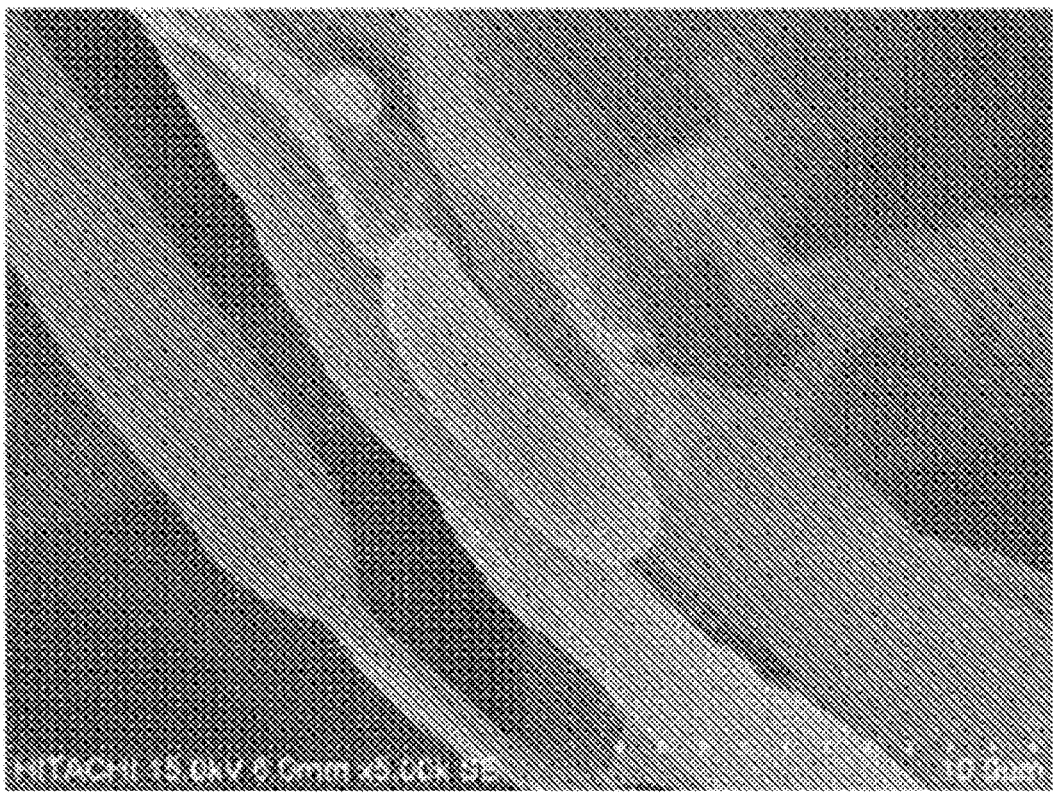
FIGS. 3A and 3B are morphological images of spores of the *D. officinale* endophytic fungus strain, *Fusarium solani* DO7, grown in PDA medium for five days in Embodiment 1, observed under SEM at different magnifications.
Figure 3B:
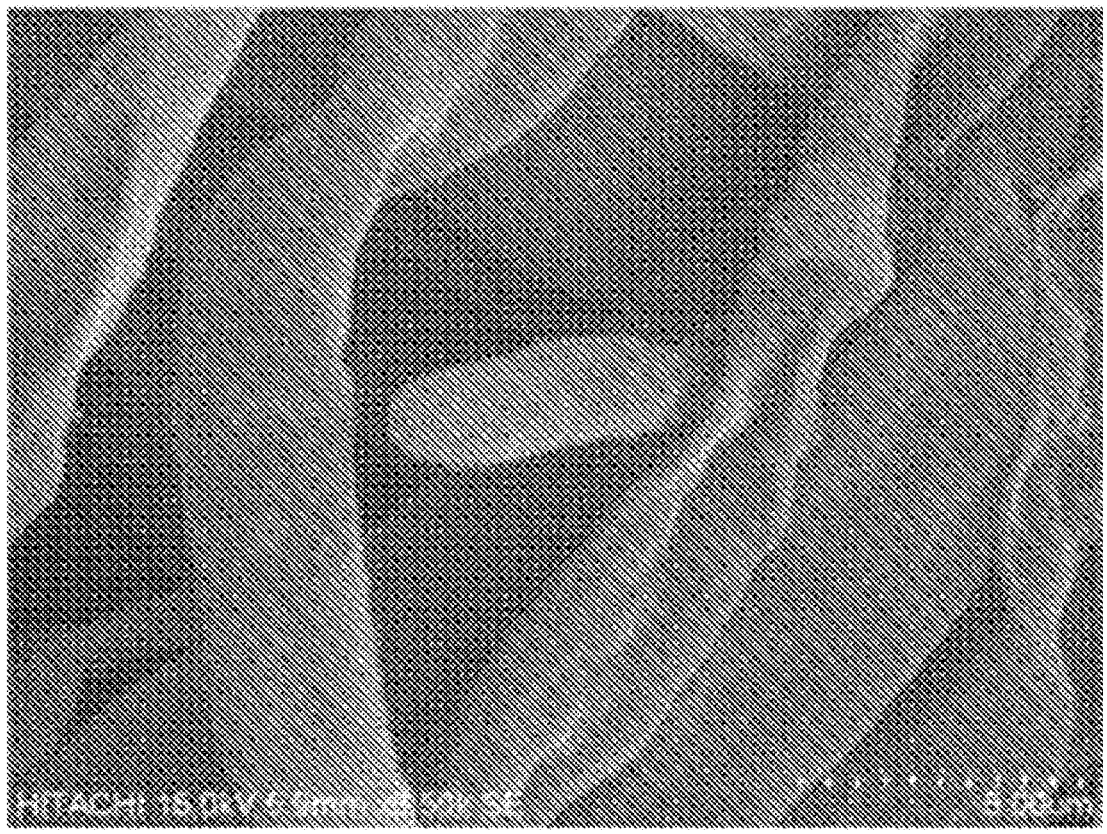

A liquid culture of the *D. officinale* endophytic fungus strain, *Fusarium solani* DO7 is characterized in that:

(1) the medium is PDB, culturing in a shaking flask for 7 days at a culture temperature of 28±1° C.; and (2) fermentation culture is characterized in that: no significant growth is observed on days 1-2 of culturing; dark red hyphae emerge on day 3 of culturing; hyphae increase on days 4-5; morphology of hyphae grown for five days, observed under microscope at 100-fold magnification, is illustrated in FIG. 1, morphology of hyphae grown for five days, observed under SEM at different magnifications, is illustrated in FIGS. 2A and 2B, and morphology of spores grown for five days, observed under SEM at different magnifications, is illustrated in FIGS. 3A and 3B;

dark red hyphae adhere to the wall of a culture flask and there are 1-2 mm dark red hyphael pellets in culture medium on day 6 of culturing;

mycelial pellets increase to 2-4 mm in size on day 7 of culturing.

Morphological characteristics of the *D. officinale* endophytic fungus strain, *Fusarium solani* DO7, comprise:

(1) asexual reproduction; dense hyphae appearing arborescent; adnation of a plurality of sporophoric sporangia, wherein a maximum of 22 spores exist; and (2) gamobium, not found.

Embodiment 2

Extraction of an extracellular polysaccharide produced by a *Dendrobium officinale* (*D. officinale*) endophytic fungus strain includes the following process:

activating a strain; culturing seed liquid; fermenting and culturing; filtering the fermented liquid under vacuum; concentrated the filtrate under vacuum; conducting alcohol precipitation on the concentrated liquid; precipitating and centrifuging; dialyzing after dissolving the precipitates in water; freezing and drying the dialysate under vacuum; and obtaining a freeze-dried powder, i.e., the extracellular polysaccharide;

Detailed extraction process includes the following steps:

(1) selecting a *D. officinale* endophytic fungus strain, *Fusarium solani* DO7, using an inoculation needle to pick up a small amount of hyphae under sterile conditions, inoculating into a test tube containing sterile solid PDA medium, and activating and culturing for 72 hours at 28±1° C.;

(2) selecting and inoculating the activated strain into a sterile liquid PDB seed medium under sterile conditions, and culturing for 72 hours on a shaking table at 28±1° C. and 120 rpm to obtain seed liquid;

(3) inoculating 10% (v/v) of the seed liquid into a 500 ml liquid medium under sterile conditions, and culturing for 7 days on a shaking table at 28±1° C. and 120 rpm;

(4) filtering fermented liquid under vacuum, concentrating a filtrate to 1/10 of volume in a rotary evaporator at 45° C., then adding 95% ethanol (v/v) corresponding to four times the volume of the concentrated liquid, oscillating vigorously, and standing for 24 hours at 4° C. to obtain alcohol deposit fluid;

(5) centrifuging the alcohol deposit fluid for 15 minutes at 8000 rpm, discarding supernatant, washing precipitates with absolute ethanol, acetone and petroleum ether sequentially, dehydrating, drying at 50° C., and then dissolving in deionized water, with a dissolved concentration of 0.2 g/mL;

(6) dialyzing precipitates dissolved in deionized water with a dialysis bag with a molecular weight cutoff of 3500 Da against distilled water for 24 hours to obtain dialysate; and (7) freezing and drying the resulting dialysate to obtain freeze-dried powders, i.e., extracellular polysaccharide produced by the *D. officinale* endophytic fungus strain, *Fusarium solani* DO7.

Yield of the extracellular polysaccharide obtained is 1.77 g/L.

Embodiment 3

Bacteriostatic test for an extracellular polysaccharide produced by a *Dendrobium officinale* (*D. officinale*) endophytic fungus strain (1) Select four common pathogenic bacteria, i.e., *Escherichia coli* (*E. coli*), *Staphylococcus aureus* (*S. aureus*), *Bacillus subtilis* (*B. subtilis*) and *Salmonella* ssp.; under sterile conditions, use an inoculation needle to pick up a small amount of colonies of each of these pathogenic bacteria, inoculate into a test tube containing sterile solid LB medium, and activate for 24 hours at 37±1° C.;

(2) select and inoculate the activated strain into a sterile liquid LB seed medium under sterile conditions, and culture for 24 hours on a shaking table at 37±1° C. and 160 rpm to obtain seed liquid;

(3) under sterile conditions, inoculate 2% (v/v) of the seed liquid into a 10 ml liquid LB plate medium, shake the plate, mix the seed liquid well with the liquid LB medium, solidify in a bechtop, and then culture for 24 hours at 37±1° C.;

(4) prepare the freeze-dried powders of the extracellular polysaccharide produced by the *D. officinale* endophytic fungus strain obtained in Embodiment 2 into a 0.05 g/l extracellular polysaccharide solution with deionized water;

(5) for an experimental group, pipette 20 ul of 0.05 g/l extracellular polysaccharide solution onto a piece of filter paper ($\Phi$=0.6 cm, sterile); for a blank control group, pipette 20 ul of sterile water onto a piece of filter paper, slightly air-dry, place in a Petri dish containing test bacteria, wherein three pieces of filter paper are placed for each species of test bacteria; and (6) incubate the prepared Petri dishes containing test bacteria in a constant temperature incubator for 24 hours at 37° C., observe and measure their zones of inhibition.

Observations of zones of inhibition are shown in TABLE 1.

Table 1. Results of antibacterial activity of the extracellular polysaccharide produced by the strain extracted in Embodiment 2

TABLE 1

| Sample/Control | Radius of the zone of inhibition (in mm) | | | |
| --- | --- | --- | --- | --- |
| | E. coli | S. aureus | B. subtilis | Salmonella ssp. |
| DO7 extracellular polysaccharide | 8.41 ± 0.21 | 10.04 ± 0.21 | 8.69 ± 0.21 | 7.33 ± 0.21 |
| Blank control | 6 ± 0.11 | 6 ± 0.12 | 6 ± 0.09 | 6 ± 0.11 |

Table 1 shows that the radii of zones of inhibition of the extracellular polysaccharide produced by the *D. officinale* endophytic fungus strain against four pathogens, including *E. coli*, *S. aureus*, *Salmonella* ssp. and *B. subtilis*, are larger than those of the blank control group, indicating that the extracellular polysaccharide produced by the *D. officinale* endophytic fungus strain plays a significant role in inhibiting common pathogenic bacteria.

It should be noted that the foregoing embodiments are merely intended for describing the technical solutions of the present invention, but not for limiting the present invention. In addition, it should be understood that those skilled in the art may make various changes and modifications after reading the present invention, and these changes and modifications and their equivalent forms shall still fall in the protection scope of the claims.

What is claimed is:

1. A method of extracting extracellular polysaccharide from a *Dendrobium officinale* endophytic fungus strain, *Fusarium solani* DO7, deposited at China Center for Type Culture Collection (CCTCC) on Mar. 27, 2017 with the accession number CCTCC NO. M2017145, comprising the following steps:
   (1) culturing the *Fusarium solani* strain DO7 in a seed liquid for fermentation;
   (2) filtering the fermented liquid from step (1) under vacuum;
   (3) vacuum-concentrating the filtrate from step (2);
   (4) alcohol-precipitating the concentrate from step (3);
   (5) centrifuging the filtrate after the precipitation in step (4);
   (6) dehydrating the precipitants after step (5) by washing with absolute ethanol, acetone and petroleum ether sequentially;
   (7) drying the washed precipitants from step (6) at 50-55° C.;
   (8) dissolving the dried precipitants from step (7) in deionized water and dialyzing; and
   (9) freeze-drying the dialysate under vacuum to obtain the extracellular polysaccharide.

2. The extraction method according to claim 1, wherein the fungus strain in step (1) is inoculated on a slant potato dextrose agar medium in a test tube, and subsequently cultured in a potato dextrose broth (PDB) for 48-72 hours at 28+/1° C. on a shaking table at 120 rpm to obtain a seed liquid; and inoculating the seed liquid at 5-15% v/v in PDB and culturing for 7-14 days at 28+/1° C. on a shaking table at 120 rpm for fermentation.

3. The extraction method according to claim 1, wherein the vacuum concentration in step (3) is to concentrate the filtrate to 1/10 of the starting volume in a rotary evaporator at 45° C.

4. The extraction method according to claim 1, wherein the alcohol precipitation in step (4) is to mix the concentrate with 95% ethanol at 1:4 volume ratio and stand for 12-24 hours at 4° C.

5. The extraction method according to claim 1, wherein the centrifugation in step (5) is at 8000 rpm for 15 minutes.

6. The extraction method according to claim 1, wherein the concentration of dissolved dried precipitants in step (8) has a range of 0.05-0.2 g/mL in deionized water; and the dialyzing step uses a dialysis bag with a molecular weight cutoff of 3500 Da against distilled water for 24-72 hours.

* * * * *

SEQUENCE LISTING

<160> NUMBER OF SEQ ID NOS: 1

<210> SEQ ID NO 1
<211> LENGTH: 572
<212> TYPE: DNA
<213> ORGANISM: Fusarium solani D07

<400> SEQUENCE: 1

```
tttcctccgg cctttgatat gcttaagttc agcgggtatt cctacctgat ccgaggtcaa      60
cattcagaag ttggggttta acggcgtggc cgcgacgatt accagtaacg agggttttac     120
tactacgcta tggaagctcg acgtgaccgc caatcaattt ggggaacgcg aattaacgcg     180
agtcccaaca ccaagctgtg cttgagggtt gaaatgacgc tcgaacaggc atgcccgcca     240
gaatactggc gggcgcaatg tgcgttcaaa gattcgatga ttcactgaat tctgcaattc     300
acattactta tcgcattttg ctgcgttctt catcgatgcc agaaccaaga gatccgttgt     360
tgaaagtttt gatttattta tggttttact cagaagttac atatagaaac agagtttagg     420
ggtcctctgg cgggccgtcc cgttttaccg ggagcgggct gatccgccga ggcaacaagt     480
ggtatgttca caggggtttg ggagttgtaa actcggtaat gatcctccgc tggttcacca     540
acggagacct tgttacgatt tttttacttc ca                                   572
```